(12) United States Patent
Portilla

(10) Patent No.: US 10,744,107 B2
(45) Date of Patent: Aug. 18, 2020

(54) METHODS OF TREATING A POIKILOTHERMIC ORGANISM IN A DECREASING TEMPERATURE ENVIRONMENT

(71) Applicant: Sixto E. Portilla, Wantagh, NY (US)

(72) Inventor: Sixto E. Portilla, Wantagh, NY (US)

( * ) Notice: Subject to any disclaimer, the term of this patent is extended or adjusted under 35 U.S.C. 154(b) by 0 days.

(21) Appl. No.: 15/434,587

(22) Filed: Feb. 16, 2017

(65) Prior Publication Data

US 2017/0239204 A1 Aug. 24, 2017

Related U.S. Application Data

(60) Provisional application No. 62/297,318, filed on Feb. 19, 2016.

(51) Int. Cl.
| | | |
|---|---|---|
| *A61K 31/202* | (2006.01) | |
| *A01K 61/20* | (2017.01) | |
| *A01K 61/10* | (2017.01) | |
| *A01K 61/54* | (2017.01) | |
| *A01K 61/59* | (2017.01) | |

(52) U.S. Cl.
CPC ............ *A61K 31/202* (2013.01); *A01K 61/10* (2017.01); *A01K 61/20* (2017.01); *A01K 61/54* (2017.01); *A01K 61/59* (2017.01)

(58) Field of Classification Search
USPC ........................................................ 514/560
See application file for complete search history.

(56) References Cited

PUBLICATIONS

Bendiksen (Effects of temperature and feed composition on essential fatty acid (n-3 and n-6) retention in Atlantic salmon (*Salmo salar* L.) parr, Fish Physiology and Biochemistry 29, 2003, pp. 133-140).*
Donaldson et al., Cold shock and fish; Journal of Fish Biology (2008) 73, 1491-1530.
Portilla, Sixto E., Mortality of first-year cultured northern quahogs, Mercenaria mercenaria, through thermal decline: Impacts of low temperature, the rate of temperature decrease and dietary 20:5n-3 and 22:6n-3, Aquaculture 454 (2016) 130-139, available online Nov. 17, 2015.
Portilla et al., Preliminary investigation into the effects of two dietary fatty acids, 20:5n-3 and 22:6n-3, on mortality of junveile Mercenaria mercenaria during the approach to winter, Aquaculture Internaltional, Journal of European Aquaculture Society , 23 (Feb. 26, 2015).

* cited by examiner

*Primary Examiner* — Kathrien A Cruz
(74) *Attorney, Agent, or Firm* — Jaksha C. Tomic. Esq.

(57) ABSTRACT

There is provided herein a method of treating a poikilothermic organism, such as marine bivalves, in a decreasing temperature environment which method comprises exposing the organism to a source of eicosapentaenoic acid (EPA) at temperatures of from 18° C. to about 12° C., and then exposing the organism to a source of docosahexaenoic acid (DHA) at temperatures of from about 11° C. to about 5° C. There is also provided herein a method of just conducting the first or second exposing step without the other, and also a method of using a decrease in temperature to catalyze the organism to produce EPA and/or DHA and/or non-methylene-interrupted fatty acids (NMIs).

20 Claims, No Drawings

METHODS OF TREATING A POIKILOTHERMIC ORGANISM IN A DECREASING TEMPERATURE ENVIRONMENT

This application claims priority to U.S. Provisional Patent Application No. 62/297,318 filed on Feb. 17, 2016, the entire contents of which are incorporated by reference herein.

FIELD OF THE INVENTION

The invention is directed to the treatment of poikilothermic organisms when they are exposed to a decreasing temperature environment. Specifically, the organisms are treated with various highly unsaturated fatty acids to avoid mortality in a decreasing temperature environment.

BACKGROUND OF THE INVENTION

Poikilothermic organisms, e.g., marine bivalves, tend to undergo reduced metabolism akin to hibernation at temperatures below 5° C. They can remain in this state using their own stored glycogen as a source of energy for anaerobic metabolism for long periods of time while suffering very low levels of mortality.

However acclimating to the declining environmental temperature is physiologically very stressful, and as a result, poikilothermic organisms such as marine bivalves, can suffer an undesirable level of mortality in a decreasing temperature environment such as the transition from the fall season to the winter season in the northern hemisphere. Certain bi-valves such as hard clams and oysters are of high market value, and excessive mortality in stocks of such bi-valves can have significant negative economic impact.

While not wishing to be bound by theory, it is presumed that in the non-limiting ease of marine bi-valves, as temperature decreases the cell-membranes of a bivalve experience changes in fluidity due to the phase transition of phospholipids which are present in the cell membranes of the bivalve. While this and various other factors can play a role in cell membrane fluidity in marine bi-valves, to more or less of an extent, these changes in fluidity of the cell membranes of the bivalve can result in increased stress levels to the bi-valve and increase the level of mortality in stocks of bivalves.

SUMMARY OF THE INVENTION

It has been surprisingly discovered by the Applicant herein that by providing poikilothermic organisms, e.g., marine bi-valves, with a properly timed source of highly unsaturated fatty acids (HUFA) such as eicosapentaneoic acid (EPA) and docosahexaenoic acid (DHA), as the temperature in the environment declines, that the mortality of the poikilothermic organisms, e.g., marine bi-valves, is significantly reduced.

More specifically, in one embodiment herein, there is provided a method of treating a poikilothermic organism in a decreasing temperature environment comprising exposing the organism to a source of eicosapentaenoic acid at temperatures of from 30° C. to about 12° C., preferably from 25° C. to about 2° C., and most preferably from about 18° C. to about 12° C., and exposing the organism to a source of docosahexaenoic acid at temperatures of from about 11.9° C. to about 0° C., and preferably from about 11.9° C. to about 5° C.

In another embodiment herein there is provided a method of treating a poikilothermic organism in a decreasing temperature environment by just exposing the organism to a source of eicosapentaenoic acid at temperatures of from 18° C. to about 12° C., or just exposing the organism to a source of docosahexaenoic acid at temperatures of from a out 11.9° C. to about 5° C.

Finally in yet another embodiment there is provided a method of treating a poikilothermic organism comprising exposing the organism to a rate of temperature decrease which provides for an increase in the rate of production of eicosapentaenoic acid and/or docosahexaenoic acid and/or non-methylene-interrupted fatty acids (NMIs).

DETAILED DESCRIPTION OF THE INVENTION

As noted above, it has been unexpectedly discovered herein that by providing poikilothermic organisms, e.g., marine bi-valves, with a source of eicosapentaneoic acid (EPA) at the initiation of a seasonal temperature decrease, and then switching to a source of docosahexaenoic acid (DHA), as the temperature in the environment continues to decline, that the mortality of the poikilothermic organisms, e.g., marine bi-valves, is significantly reduced before they undergo reduced metabolism akin to hibernation at temperatures below 5° C.

Other than in the working examples or where otherwise indicated, all numbers expressing amounts of materials, reaction conditions, time durations, quantified properties of materials, and so forth, stated in the specification and claims are to be understood as being modified in all instances by the term "about" whether or not the term "about" is used in the expression.

It will be understood that any numerical range recited herein includes all sub-ranges within that range and any combination of the various endpoints of such ranges or sub-ranges, be it described there or anywhere else in the specification.

It will also be understood herein that any of the components of the invention herein as they are described by any specific genus or species, can he used in one embodiment to define an alternative respective definition of any endpoint of a range elsewhere described in the specification with regard to that component, and can thus, in one non-limiting embodiment, be used to supplant such a range endpoint, elsewhere described.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

Reference is made to substances, components, or ingredients in existence at the time just before first contacted, formed in situ, blended, or mixed with one or more other substances, components, or ingredients in accordance with the present disclosure. A substance, component or ingredient identified as a reaction product, resulting mixture, or the like may gain an identity, property, or character through, a chemical reaction or transformation during the course of contacting, in situ formation, blending, or mixing operation if conducted in accordance with this disclosure with the application of common sense and the ordinary skill of one in the relevant art (e.g., chemist). The transformation of chemical reactants or starting materials to chemical products or final materials is a continually evolving process, independent of the speed at which it occurs. Accordingly, as, such a transformative process is in progress there may be a mix of starting and final materials, as well as intermediate species that may be, depending on their kinetic lifetime, easy or difficult to detect with current analytical techniques known to those of ordinary skill in the art.

Reactants and components referred to by chemical name or formula in the specification or claims hereof, whether referred to in the singular or plural, may be identified as they exist prior to coining into contact with another substance referred to by chemical name or chemical type (e.g., another reactant or a solvent). Preliminary and/or transitional chemical changes, transformations, or reactions, if any, that take place in the resulting mixture, solution, or reaction medium may be identified as intermediate species, master batches, and the like, and may have utility distinct from the utility of the reaction product or final material. Other subsequent changes, transformations, or reactions may result from bringing the specified reactants and/or components together under the conditions called for pursuant to this disclosure. In these other subsequent changes, transformations, or reactions the reactants, ingredients, or the components to be brought together may identify or indicate the reaction product or final material.

The expression "poikilothermic organism" as used herein can encompass types of vertebrate animals, specifically fish, e.g., shellfish, amphibians, and reptiles, as well as a large number of invertebrate animals. In, one embodiment herein a "poikilothermic organism" can be a marine organism, such as the non-limiting example of a marine bivalve organism, such as those selected from the group consisting of clams, such as "surf" clams or "mano" clams (also known as "steamers"), mussels, oysters, scallops, shrimp, brine shrimp, prawns (such as macrobrachum prawns), lobsters (such as spiny and spanish or slipper lobsters), crayfish and crabs (such as crabs selected from the group consisting of king crab, stone crab, rock crab, dungeness crab, snow crab, and blue crab), krill, squid, cuttlefish, octopus, copepods, zoo plankton, and the like.

The expression "decreasing temperature environment" can be directed to air temperature or water temperature, e.g., sea water temperature, and can in one non-limiting embodiment comprise the temperature transition from a summer season to the completion of the winter season, such as a transition from fall to spring in the northern hemisphere. In a more specific embodiment the decreasing temperature environment can be a decreasing sea water temperature environment of from 40° C. down to 0° C., more specifically from 35° C. down to 5° C. and even more specifically from 25° C. down to 5° C. and most specifically from 20° C. down to 5° C. In some specific embodiments herein the decreasing temperature environment is such that the rate of temperature decrease is greater than 0.25° C. per day, and more specifically from about 0.6° C. per day to about 2.1° C. per day. It will be understood herein that these rates of temperature decrease described herein can be used as the rate of temperature decrease necessary to provide for an increase in the rate of production of EPA and/or DHA and/or ion-methylene-interrupted fatty acids, as is, described in the further embodiments described herein. In one embodiment such a rate of increase can be from about 5% to about 100%, preferably from about 10% to about 50% rate of increase as compared to when the method(s) described herein are not conducted.

As described herein the EPA can be an un-substituted EPA. Likewise, the DHA described herein can be an in-substituted DHA.

The "source" of EPA and DHA described herein can comprise any conventional or commercially available source, but in one non-limiting embodiment the source of EPA and/or DHA can be provided by algae containing the EPA and/or DHA. Some examples of algae which contain high levels of EPA which may be suitable herein can be *Thalassiosira weissflogii*. Some examples of algae which contain high levels of DHA which may be suitable herein can be *Isochrysis galbana* and *Prorocenturm minimum*. In one non-limiting embodiment the source of EPA and/or DHA can be other than an algae source but can be provided in the form of EPA and/or DHA alone, provided it is provided in the amounts recited herein for the source of algae(s) described herein. In one embodiment the amount of EPA and/or DHA can be from about 0.001 µmol/100 ml, preferably from about 0.15 µmol/100 ml to about 0.005 µmol/100 ml, and most preferably from about 0.01 µmol/100 ml to about 0.015 µmol/100 ml.

Based on the type of algae employed in the method herein, the concentration of EPA and/or DHA in these algae can vary considerably, but in one embodiment a useful concentration of EPA can be greater than 10% total molar composition of fatty acids of the algae, preferably greater than 18% total molar composition of fatty acids of the algae, more specifically from about 17% to about 18% total molar composition of fatty acids of the algae. In another embodiment a useful concentration of DHA can be greater than 10% total molar percent composition of fatty acids of the algae, more specifically from about 11% to about 26% total molar percent composition of fatty acids of the algae.

In one non-limiting embodiment herein the amount of EPA and/or DHA employed, in the method(s) described herein is such that in a sea water environment the amount of EPA and/or DHA is at least 0.001 µmol/100 ml, preferably from about 0.15 µmol/100 ml to about 0.005 µmol/100 ml, and most preferably from about 0.01 µmol/100 ml to about 0.015 µmol/100 ml.

When the method described herein is conducted, the sum level of EPA and any non-methylene interrupted (NMI) fatty acids at temperatures of above 12° C. is preferably above 7.0%, total level of EPA and any NMI fatty acids that exist before the method is applied. When the range of temperature decrease is greater than 12° C. the dietary molar % of EPA is greater than the dietary molar % of DHA.

As described above, the method herein can comprise exposing the poikilothermic organism to a source of eicosapentaenoic acid at temperatures of from 18° C. to about 12° C., and exposing the organism to a source of docosahexaenoic acid at temperatures of from about 11.1° C. to about 5° C. In another embodiment herein the method can comprise exposing the organism to a source of eicosapentaenoic acid at temperatures of from 30° C. to about 12° C., and exposing the organism to a source of docosahexaenoic acid at temperatures of from about 11.9° C. to about 5° C. In yet another embodiment herein, the method can comprise exposing the organism to a source of eicosapentaenoic acid at temperatures of from 20° C. to about 12° C., and exposing the organism to, a source of docosahexaenoic acid at temperatures of from about 11.9° C. to about 5° C. It will be understood herein that the reference to "about 12° C." and "about 11.9° C." are such that they are reflective of points in a decreasing temperature environment herein, such that the method can comprise use of EPA until 12.0° C. and then a use of DHA for temperatures less than 12° C., e.g., 11.9° C. and below and as described herein.

It is preferable herein that during the step of exposing the organism to a source of EPA that the organism not be exposed to a source of DHA, or at the very least, no more than 4.0% DHA of total molar composition of fatty acids in the source of EPA, preferably, no more than 2.0% DHA of total molar composition of fatty acids in the source of EPA and most preferably, zero % MA of total molar composition of fatty acids in the source of EPA, Likewise, during the step of exposing the organism to a source, of DHA that the organism not be exposed to a source of EPA, or at the very least, no more than 4.0% EPA of total molar composition of fatty acids in the source of DHA preferably, no more than 2.0% EPA of total molar composition of fatty acids in the sourer of DHA and most preferably, zero % EPA of total molar composition of fatty acids in the source of DHA.

In a further embodiment herein following and or during the second exposing step of the method described herein, the organism is stored at a temperature of from 2° C. to about 4° C.

The decreasing temperature environment described herein, when present as a sea water environment, can have, a level of dissolved oxygen present in the sea water which is conducive to survival of poikilothermic organisms such as marine bi-valves. Such a level of dissolved oxygen can be from about 2 to about 9 mg/L, more specifically from about 4 to about 8 mg/L and most specifically from about 5 to about 7 mg/L.

In accordance with the method(s) described herein, by decreasing the temperature according to the method(s) described herein, there will be an increase in the omega-3 fatty acid values, concomitant to the magnitude of temperature decrease, in the bivalves' biomass, and as a result will produce greater levels of omega-3s in the bivalve for the human consumers' diet as compated to if the method(s) described herein bad not been conducted. As a result, there will be an increase in the market value of the shellfish subject to method(s) described herein, especially during the summer months when the magnitude of temperature decrease from warm environmental temperatures to cool refrigeration (e.g., 25 deg C. to 3 deg C.) is highest. It will be understood herein that the attached journal references *Preliminary investigation into the effects of two dietary fatty acids, 20:5n-3 and 22:6n- 3, on mortality of juvenile Mercenaria mercenaria during the approach to winter*, Portilla et al., Aquaculture International, Journal of the European Aquaculture Society, Feb. 26, 2015, and *Mortality of first-year cultured northern quahogs, Mercenaria mercenaria, through thermal decline: Impacts of low temperature, the rate of temperature decrease and dietary 20:5n-3 and 22:6n-3*, Sixto E Portilla, Aquaculture, Nov. 17, 2015, and *Survival of juvenile northern quahogs during seasonal temperature decline likely a function of diet and NMI-fatty acid synthesis* Journal of Applied Aquaculture, Apr. 26, 2016 are incorporated by reference herein in their entireties.

While the invention has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be hunted to the particular embodiments disclosed as the best mode contemplated for carrying out this invention but that the invention will include Edi embodiments falling within the scope of the appended claims.

The invention claimed is:

1. A method of treating a poikilothermic organism in a decreasing temperature environment comprising:
   exposing the organism to a source of eicosapentaenoic acid in a decreasing temperature environment which is decreasing in temperature from 30° C. to about 12° C., and
   exposing the organism to a source of docosahexaenoic acid in a decreasing temperature environment which is decreasing in temperature from about 11.9° C. to about 0° C. and wherein the mortality of the poikilothermic organisms is reduced compared to the mortality of identical poikilothermic organisms which are not exposed to a source of eicosapentaenoic acid in a decreasing temperature environment which is decreasing in temperature from 30° C. to about 12° C. and docosahexaenoic acid in a decreasing temperature environment which is decreasing in temperature from about 11.9° C. to about 0° C.

2. The method of claim 1 wherein the poikilothermic organism is a marine organism.

3. The method of claim 1 wherein the poikilothermic organism is a marine bivalve organism.

4. The method of claim 1 wherein the poikilothermic organism is any one of a clam, a mussel, an oyster, a scallop.

5. The method of claim 1 wherein the decreasing temperature environment occurs from a transition from fall to winter in the northern hemisphere.

6. The method of claim 1 wherein the decreasing temperature environment is a decreasing sea water temperature environment decreasing from 40° C. down to −1.0° C.

7. The method of claim 1 wherein the source of eicosapentaenoic acid is an algae containing the eicosapentaenoic acid in a molar amount greater than 10% total composition of the algal fatty acids.

8. The method of claim 7 wherein the algae is *Thalassiosira weissflogii*.

9. The method of claim 1 wherein the source of docosahexaenoic acid is an algae containing the docosahexaenoic acid in a molar amount greater than 10% total composition of the algal fatty acids.

10. The method of claim 9 wherein the algae is selected from the group consisting of *Isochrysis galbana, Prorocenturm minimum* and combinations thereof.

11. The method of claim 7 wherein during the step of exposing the organism to a source of eicosapentaenoic acid the organism is exposed to no more than 4% docosahexaenoic acid of total composition of fatty acids.

12. The method of claim 9 wherein during the step of exposing the organism to a source of docosahexaenoic acid the organism is exposed to no more than 4% eicosapentaenoic acid of total composition of fatty acids.

13. The method of claim 1 wherein following and/or during the second exposing step the organism is stored at a temperature of from 2 to 4° C. for a period of from about 1 day to about 3 months.

14. The method of claim 1 wherein the method occurs in a sea water environment with a level of dissolved oxygen of from about 5 mg/L to about 7 mg/L.

15. The method of claim 1 wherein the method occurs in a sea water environment with a sum level of eicosapentaenoic acid and any non-methylene interrupted fatty acids of greater than 10% total molar composition of fatty acids in the sea water environment.

16. A method of treating a poikilothermic organism in a decreasing temperature environment comprising exposing the organism to a source of eicosapentaenoic acid at temperatures of from 25° C. to about 12° C. or, exposing the organism to a source of docosahexaenoic acid at temperatures of from about 11.9° C. to about 5° C.

17. A method of treating a poikilothermic organism comprising exposing the organism to a rate of temperature decrease which provides for an increase in the rate of production of eicosapentaenoic acid and/or docosahexaenoic acid and/or non-methylene interrupted fatty acids.

18. The method of claim 1 wherein the poikilothermic organism is selected from the group consisting of fish, shrimp and crabs.

19. The method of claim 18 wherein the poikilothermic organism is a fish.

20. A method of treating a poikilothermic organism in a decreasing temperature environment consisting of:

exposing the organism to an algae containing the eicosapentaenoic acid in a molar amount greater than 10% total composition of the algal fatty acids in a decreasing temperature environment which is decreasing in temperature from 30° C. to about 12° C. and wherein the organism is exposed to no more than 4% docosahexaenoic acid of total composition of fatty acids in this step, and exposing the organism to an algae containing the docosahexaenoic acid in a molar amount greater than 10% total composition of the algal fatty acids in a decreasing temperature environment which is decreasing in temperature from about 11.9° C. to about 5° C. and wherein the organism is exposed to no more than 4% eicosapentaenoic acid of total composition of fatty acid in this step, and wherein the mortality of the poikilothermic organisms is reduced compared to the mortality of identical poikilothermic organisms which are not exposed to a source of eicosapentaenoic acid in a decreasing temperature environment which is decreasing in temperature from 30° C. to about 12° C. and docosahexaenoic acid in a decreasing temperature environment which is decreasing in temperature from about 11.9° C. to about 0° C.

* * * * *